US00PP28761P2

(12) United States Plant Patent
McCracken

(10) Patent No.: US PP28,761 P2
(45) Date of Patent: Dec. 12, 2017

(54) ***EUPHORBIA* PLANT NAMED 'GALAXY GLOW'**

(50) Latin Name: ***Euphorbia* hybrid**
Varietal Denomination: Galaxy Glow

(71) Applicant: Thomas Patrick McCracken, Zebulon, NC (US)

(72) Inventor: Thomas Patrick McCracken, Zebulon, NC (US)

( * ) Notice: Subject to any disclaimer, the term of this patent is extended or adjusted under 35 U.S.C. 154(b) by 0 days.

(21) Appl. No.: 15/330,128

(22) Filed: Aug. 11, 2016

(51) Int. Cl.
*A01H 5/02* (2006.01)

(52) U.S. Cl.
USPC ..... Plt./302

(58) Field of Classification Search
USPC ..... Plt./302
See application file for complete search history.

*Primary Examiner* — Annette Para
(74) *Attorney, Agent, or Firm* — Penny J. Aguirre

(57) ABSTRACT

A new cultivar of *Euphorbia* plant named 'Galaxy Glow' that is characterized by its very compact plant habit, its blooming period in April to June in North Carolina, its flowering bracts that retain color for a long period, its flower bracts that are rose pink in color, its young foliage that is strongly flushed with rose and purple colors and its inflorescences that are large in size.

3 Drawing Sheets

Botanical classification: *Euphorbia* hybrid.
Varietal denomination: 'Galaxy Glow'.

BACKGROUND OF THE INVENTION

The present invention relates to a new and distinct cultivar of *Euphorbia* of hybrid origin and will be referred to hereafter by its cultivar name, 'Galaxy Glow'. 'Galaxy Glow' represents a new herbaceous perennial grown for landscape and container use.

The new cultivar was discovered as a chance seedling by the Inventor in spring of 2000 growing outdoors in his garden in Zebulon, N.C. The parents of the new cultivar are unknown, however *Euphorbia characias* ssp. *characias* 'Humpty Dumpty' (not patented) is thought to be the female parent and *Euphorbia dulcis* 'Chameleon' (not patented) is thought to be the male parent based on their proximity to the discovered seedling and the characteristics of the new cultivar. The seedling was found underneath a plant of 'Humpty Dumpty' and is therefore thought to be the seed parent. by Asexual propagation of the new cultivar was first accomplished by stem cuttings by the Inventor in summer of 2003 in Zebulon, N.C. Asexual propagation by stem cuttings has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Galaxy Glow' as a new and unique cultivar of *Euphorbia*.

1. 'Galaxy Glow' exhibits a very compact plant habit.
2. 'Galaxy Glow' exhibits very heavy basal branching.
3. 'Galaxy Glow' exhibits a blooming period in April to June in North Carolina.
4. 'Galaxy Glow' exhibits flowering bracts that retain color for a long period.

5. 'Galaxy Glow' exhibits flower bracts that are rose pink in color.
6. 'Galaxy Glow' exhibits young foliage that is strongly flushed with rose and purple colors.
7. 'Galaxy Glow' exhibits inflorescences that are large in size.

'Humpty Dumpty', the propable female parent plant of 'Galaxy Glow', is similar to 'Galaxy Glow' in having a compact plant habit. 'Humpty Dumpty' differs from 'Galaxy Glow' in having foliage that is blue-green in color, flowering bracts that are yellow-green in color with the coloration held for a shorter period, and in blooming earlier in the season. 'Chameleon', the probable male parent plant of 'Galaxy Glow' is similar to 'Galaxy Glow' in having foliage that is flushed with a purple color. 'Chameleon' differs from 'Galaxy Glow' in having foliage that is flushed with a darker and more purple color, lacks the rose pink fluch on the flower bracts, and has less basal branching. 'Galaxy Glow' can be most closely compared to the *Euphorbia characias* ssp. *characias* cultivar 'Blue Hills' (not patented). 'Blue Hills' is similar to 'Galaxy Glow' in having inflorescences that are large in size. 'Blue Hills' differs from 'Galaxy Glow' in having leaves that are blue-green in color, a larger plant size, and flower bracts that are yellow in color.

BRIEF DESCRIPTION OF THE DRAWINGS

The accompanying colored photographs illustrate the overall appearance and distinct characteristics of the new *Euphorbia*. The photographs were taken of plants 1 year in age as grown in a two-gallon container in Zebulon, N.C.

Figure 1:
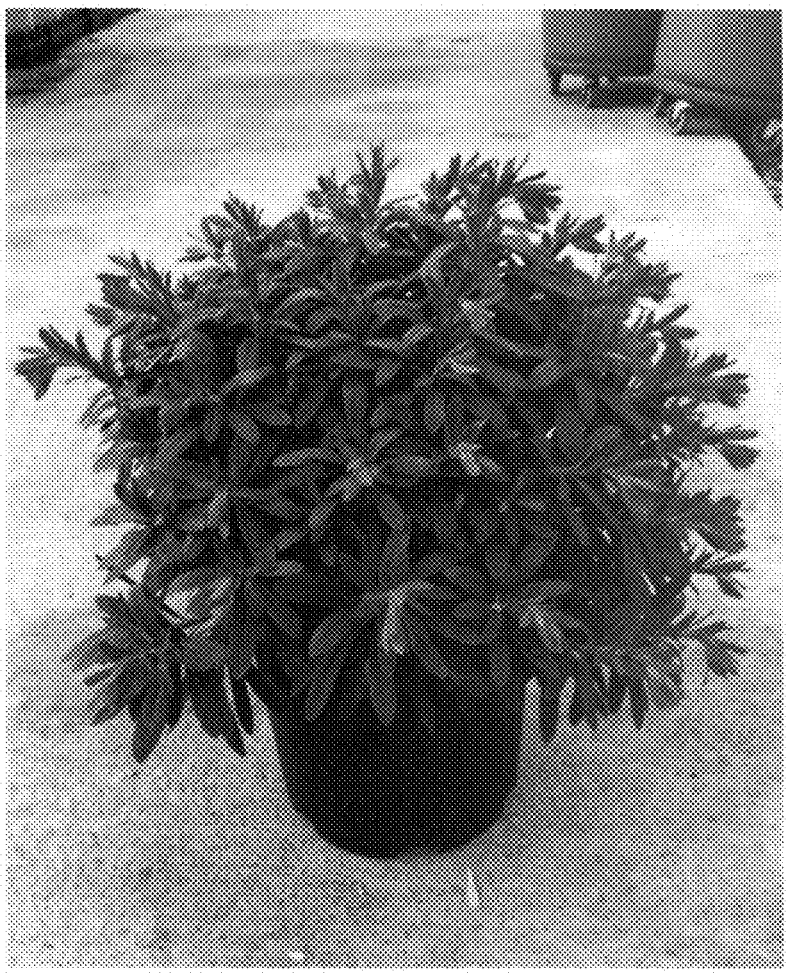
FIG. 1 provides a side view of the plant habit and foliage coloration of the growing tips in spring of 'Galaxy Glow'.
Figure 2:
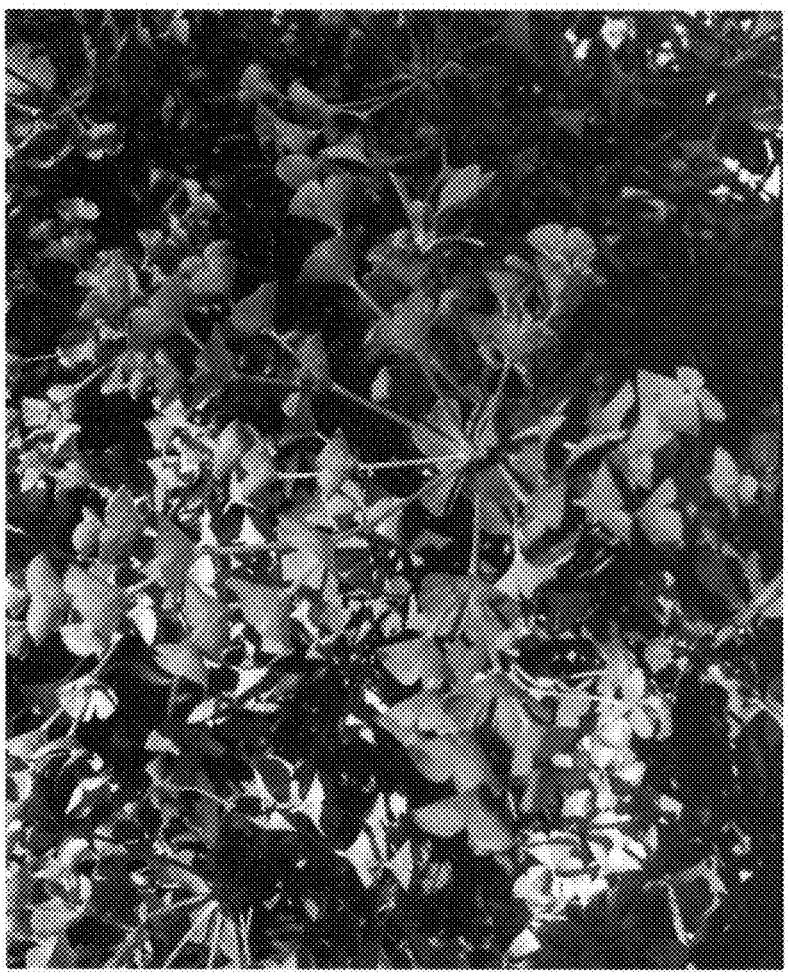

The photograph in FIG. 2 provides a close-up view of the flower bracts of 'Galaxy Glow' in early summer.

Figure 3:
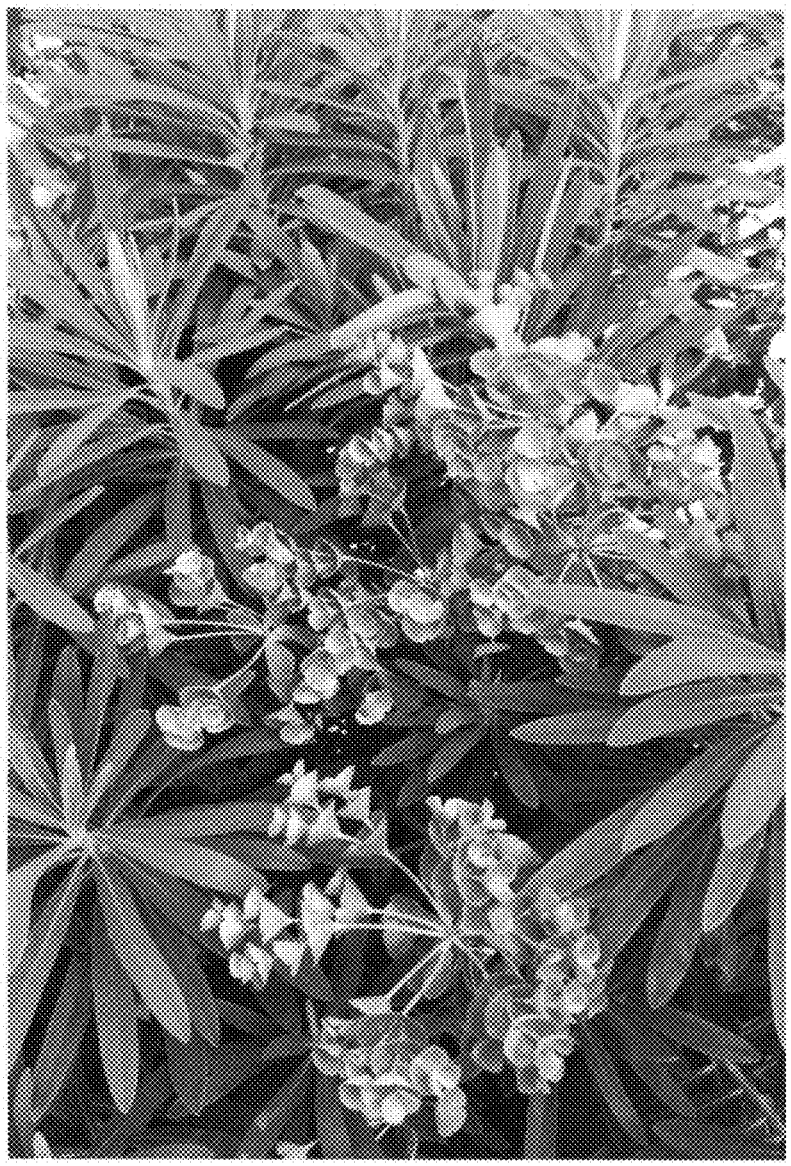

The photograph in FIG. 3 provides a view of the foliage and flower bracts of 'Galaxy Glow' in late summer.

The colors in the photographs are as close as possible with the photographic and printing technology utilized and the color values cited in the detailed botanical description accurately describe the colors of the new *Euphorbia*.

DETAILED BOTANICAL DESCRIPTION OF THE PLANT

The following is a detailed description of 1 year-old plants of the new cultivar as grown outdoors in a two-gallon container in Zebulon, N.C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—April to June in Zebulon, N.C.

*Plant type*.—Herbaceous perennial.

*Plant habit*.—Upright, compact and globular, inverted triangular shape.

*Height and spread*.—An average of 53 cm in height and 45 cm in width.

*Cold hardiness*.—At least to U.S.D.A. Zones 6 to 8.

*Diseases and pests*.—No susceptibility or resistance to diseases or pests has been observed, has been observed to be disease free.

*Root description*.—Fine, fibrous, 161A in color.

*Root development*.—Average of 20 days at temperatures of 20° C. to initiate roots and a young rooted plant is produced in about 2 months.

*Propagation type*.—Stem cuttings.

*Growth rate*.—Vigorous.

*Vigor*.—Strong.

Stem description:

*Stem shape*.—Rounded.

*Stem color*.—145B from base to upper mid-section, 145A at the top section, slightly flushed with 59A, previous season's wood (typically cut clean); a blend of N200C, 199A, and 201A.

*Stem size*.—Lateral branches; 45 cm in length and 6 mm in width.

*Stem surface*.—Young stems; densely to moderately covered with pubescent hair that matches the surface color and are 0.5 mm in length, mature stems; slightly glossy and smooth, moderately covered with bundle scars, an average of 22 scars per stem, linear in shape and 183A in color, old wood; rugose and dull.

*Stem aspect*.—Ranging between being held upright (90°=vertical) and bowing out at the center and growing inward at the top, shorter stems held at an angle of 30° (90°=vertical).

*Stem strength*.—Flexible but strong.

*Stem characteristics*.—When broken, stems produce a milky, latex-like sap, NN155D in color.

*Internode length*.—An average of 1 cm at mid stem.

*Branching habit*.—Freely branching, very densely branched, lateral branches develop from crown, an average of 120 lateral branches.

Foliage description:

*Leaf shape*.—Linear-oblanceolate.

*Leaf division*.—Simple.

*Leaf base*.—Attenuate.

*Leaf apex*.—Acute with small mucronate tip.

*Leaf venation*.—Pinnate, mid rib on lower section of upper surface and mid rib of lower surface 144B in color, other veins match leaf coloration.

*Leaf margins*.—Entire and densely covered with minute downy hairs NN155C in color, less than 0.5 mm in length.

*Leaf attachment*.—Sessile.

*Leaf arrangement*.—Whorled.

*Leaf surface*.—Young and mature leaves upper surface; satiny, densely covered with downy hairs that match the leaf color and <0.5 mm in length, young mature leaves lower surface; dull, tomentose.

*Leaf sap*.—When broken, mid-vein produces a milky, latex-like sap, NN155D in color.

*Leaf color*.—Young growing tips; 61B to 61C, young leaves upper surface; 147A, young leaves lower surface; 178A, mature leaves upper surface; 139A, mature leaves lower surface; 138A and suffused with 178A.

*Leaf number*.—Average of 50 per lateral branch.

*Leaf size*.—Up to 12 cm in length and 1.5 cm in width.

Flower description:

*Inflorescence type*.—Umbel-like compound terminal cyme with single cymes on lower axils.

*Flower fragrance*.—None.

*Inflorescence*.—Average of 10 days.

*Inflorescence size*.—27 cm in length and 10 cm in width with individual cymes an average of 2.5 cm in height and width.

*Flower type*.—Cyathium comprised of a cup-shaped involucre surrounding nectary, a female flower and reduced male flowers, asepalous and apetalous.

*Cyathia quantity*.—Average of 37 per lateral stem.

*Cyathia aspect*.—Held straight outward to drooping.

*Cyathia size*.—An average of 1.5 cm in depth and 1 cm in diameter.

*Peduncles*.—An average of 8 per terminal compound cyme and one per axillary cymes, an average of 4 cm in length and 1 mm in width, held in an average angle of 60° (90°=vertical), low strength, 145A in color with slight blush of 178B, surface is dull and densely covered with pubescent hairs that match surface color and are 1 mm in length.

*Pedicels* (*stem of cyathia*).—An average of 2 per peduncle, average of 7 mm in length and 1 mm in width, held slightly outward to downward in an average angle of 40° (90°=vertical), low strength, 145A in color, surface is dull and densely covered with pubescent hairs that match surface color and are 1 mm in length.

*Nectaries*.—4 per cyathia, flattened crescent shaped glands each with 2 narrowly acute tips fused into the base of the flower, 2 mm in length and width, outer surface is 144B flushed with slight hues of 182A, tips and minute center are 11D in color, inner surface N144A, outer surface is very glossy and rubbery, inner surface is dull.

*Floral bracts*.—2 opposite at base of cymes, mirrored, orbicular in shape, rounded and slight cuspidate apex, fused base, inner and outer glabrous and smooth surfaces, entire margins, 143A in color, 6 in whorl at base of terminal compound cyme; an average of 6, upper surface color; when young a blend of 139A and 138A, when in bloom and into summer 39A and 138A and suffused with a blend of 63B and 64B, lower surface color; when young 138A, when opening and into summer; a blend of 63B and 64B, coloration in late summer becomes less suffused on both surfaces, 1.5 cm in length and 1 cm in width, both surfaces are glabrous, obovate in shape, cuneate base, round apex with very small cuspidate tip.

*Involucral bracts.*—2, upper surface color; a blend of 139A and 138A, lower surface color; 138A, 1.5 cm in length and 1 cm in width, both surfaces are glabrous.

Reproductive organs:

*Gynoecium.*—One per central female flower (apetalous and asepalous), pistil 3-parted with bifid stigmas an average of 6 mm in length and 0.7 mm in with and 145C in color, style 1 mm in width and 145C in color, ovary; urn-shaped shape, 2.5 mm in length, 2 mm in diameter and 145C in color, pubescent surface.

*Androecium.*—An average of 4 reduced stamens, oval in shape and bi-lobed, 1 mm in length, 145D in color, no pollen was observed.

*Fruit/seed.*—No fruit or seed has been observed.

It is claimed:

1. A new and distinct cultivar of *Euphorbia* plant named 'Galaxy Glow' as herein illustrated and described.

* * * * *